United States Patent [19]
Gee et al.

[11] Patent Number: 5,872,243
[45] Date of Patent: Feb. 16, 1999

[54] CAGED NUCLEOTIDES

[75] Inventors: Kyle R. Gee, Springfield, Oreg.; Hon Cheung Lee, Woodbury; Robert Aarhus, Brooklyn Park, both of Minn.; Richard P. Haugland, Eugene, Oreg.; Timothy F. Walseth, Roseville; Richard M. Graeff, St. Paul, both of Minn.

[73] Assignees: Molecular Probes, Inc., Eugene, Oreg.; The Regents of the University of Minnesota, Minneapolis, Minn.

[21] Appl. No.: 497,183

[22] Filed: Jun. 30, 1995

[51] Int. Cl.$^6$ .............................. C07H 1/00; C07H 21/00
[52] U.S. Cl. .................. 536/26.23; 536/25.6; 536/26.2; 536/26.21; 536/26.22; 536/26.71; 536/123.13; 536/124; 536/127
[58] Field of Search ................................. 514/45, 46, 47; 536/26.24, 25.6, 26.23, 124, 127, 26.2, 26.21, 26.22, 26.71, 123.13

[56] References Cited

U.S. PATENT DOCUMENTS

| | | |
|---|---|---|
| 4,849,362 | 7/1989 | DeMarinis et al. . |
| 5,393,667 | 2/1995 | Strumwasser et al. . |
| 5,635,608 | 6/1997 | Haugland et al. . |

OTHER PUBLICATIONS

Walker, et al., Biochemistry 28, 3272 (1989).
Schultz, et al., J. Biol. Chem. 268, 6316 (1993).
Graeff, et al., J. Biol. Chem. 269, 30260 (1994).
Walseth, et al., Biochim. Biophys. Acta 1178, 235 (1993).
Lee, et al., J. Biol. Chem. 270, 2152 (1995).
Lee, et al., Cell Regulation 2, 203 (1991).
Gu, et al., J. Am. Chem. Soc. 116, 7481 (1994).
Yamada, et al., J. Am. Chem. 116, 10787 (1994).
Givens, et al., J. Am. Chem. Soc. 114, 8708 (1992).
Ramesh, et al., Proc. Nat. Acad. Sci. 90, 11074 (1993).
Walker, et al., J. Am. Chem. Soc. 110, 1710 (1988).
Lee, et al., J. Biol. Chem. 264, 1608 (1989).
Clapper, et al., J. Biol. Chem 262, 9561 (1987).
Lee, J. Biol. Chem. 268, 293 (1993).
Lee, et al., Science 261, 352 (1993).
Dargie, et al., Cell Regulation 1, 279 (1990).
Lee, et al., Vitamins and Hormones 48, 199 (1994).
Chini, et al., J. Biol. Chem. 270, 3216 (1995).
Aarhus, et al., J. Biol. Chem. 270, 7745 (1995).

*Primary Examiner*—James O. Wilson
*Attorney, Agent, or Firm*—Allegra J. Helfenstein; Anton E. Skaugset

[57] ABSTRACT

The present invention describes a family of photolabile caged nucleotides, including cyclic nucleotides. The compounds of the present invention are caged analogs and derivatives of NAD$^+$, NADH, NADP, NADPH, NAADP and cADPR. The photolysis of the present compounds allows the release of the free nucleotide in vivo or in vitro with precise spatial and temporal control. The compounds are useful for the photolytic generation of free nucleotides in aqueous samples, for example, in the study of calcium mobilization in cells and cell homogenates.

27 Claims, 3 Drawing Sheets

CAGED NUCLEOTIDES

This invention was made with government support under grants HD17484 and HD32040 from the National Institutes of Health. The government has certain rights in the invention.

FIELD OF THE INVENTION

The present invention describes a family of photolabile caged nucleotides, including cyclic nucleotides. The compounds of the present invention are caged analogs and derivatives of $NAD^+$, NADH, NADP, NADPH, NAADP and cADPR. The photolysis of the present compounds allows the release of the free nucleotide in vivo or in vitro with precise spatial and temporal control. The compounds are useful for the photolytic generation of free nucleotides in aqueous samples, for example, in the study of calcium mobilization in cells and cell homogenates.

BACKGROUND OF THE INVENTION

Covalent attachment of a photoremoveable group to a parent compound (i.e. "caging") to alter its physical or biological properties has been exploited extensively for following components of dynamic systems. The term "cage" refers to a photolytically sensitive substituent that is designed to interfere with the reactivity or other physical properties of the free probe. Photolysis (typically by illumination in the UV (250–400 nm) region of the spectrum) cleaves the caging group, restoring the normal properties of the parent compound. In this way it is possible to release the parent compound into the system of interest with much better temporal and spatial resolution than is possible by simple diffusion.

Appropriate caging groups for compounds used in the study of processes that change rapidly, such as biological processes, must be photolyzed rapidly and with relatively high quantum yield. It is also important that caging alters some property of the parent compound to the desired level, and that the caged compound is stable and still soluble in the system of interest. A variety of caged probes exist, including caged nucleotides. For example, the o-nitrobenzyl group and its substituted variants have been used to cage nucleotide phosphates at the terminal phosphate. The o-nitrobenzyl group has also been used to cage a non-nucleotide phosphate, e.g. on the calcium ion mobilizer 1,4,5-inositol triphosphate ($IP_3$). The preparation of the caged $IP_3$, however, is difficult and technically demanding (Walker et al., BIOCHEMISTRY 28, 3272 (1989)). Specifically, the preparation of caged $IP_3$ yields varying quantities of seven or more possible products, only two of which possess the desired biological properties required to function as a caged calcium ion mobilizer. These two products must then be isolated by preparative HPLC in a tedious process that requires the use of radioactive $IP_3$ as a means of monitoring product purity.

In contrast, the caged nucleotides of this invention are relatively straightforward to prepare. Caged analogs of nicotinamide adenine dinucleotide (NAD) or derived from NAD, such as nicotinamide adenine dinucleotide phosphate (NADP), nicotinic acid adenine dinucleotide phosphate (NAADP) and cyclic-adenine dinucleotide phosphate ribose (cADPR) can in most cases be prepared by a single reaction, followed by rapid purification in water, which allows for quick isolation of preparative quantities of the caged agent. This facile synthesis is a marked improvement over the necessity of preparing caged $IP_3$. The caged calcium-mobilizing agents of the invention have other advantages as well. Whereas the parent compounds must be added to living cells by microinjection, potentially resulting in nonspecific $Ca^{2+}$ release due to cell leakage and/or damage; triggering the induction of $Ca^{2+}$ release using photolysis of a probe such as caged cADPR eliminates possible injection artifacts. Similarly, inadvertent elevation of $Ca^{2+}$ in the cell is easily recognized since only normal physiological $Ca^{2+}$ changes are observed prior to photolysis of the caged mobilizer. In addition, since the caged agent is inactive until photolyzed, it can be added to cells by methods other than microinjection, resulting in less cell damage, or allowing the cell to recover before performing a measurement. In particular, specific versions of caged agents may be selected so as to allow addition of the nucleotide to cells by passive penetration of the probe through the cell's membrane.

Calcium ion mobilization is just one of a number of biological processes that can be studied using caged nucleotides. In addition to the analogs and derivatives of NAD that exhibit varying degrees of biological activity as calcium mobilizers, substitution of cADPR at the 8-position by amino, bromo or azido groups, results in compounds that act as antagonists for cADPR. Selected related nucleotides where the purine base adenine is replaced with other purines or pyrimidines, or where the ribosyl sugar is replaced by deoxyribosyl, are useful as fluorescent probes for NAD cyclase activity, or for the study of other poorly explored biological responses in cellular systems. Furthermore, NAD undergoes reduction to yield NADH, and this redox pair represents the primary electron carrier system in living systems. The present invention describes caged nucleotides that can be used to study the physiological effects of the free nucleotide in biological systems, including cells, cell extracts and cell homogenates. The use of a chemically caged nucleotide allows the free nucleotide to be produced within the biological sample with precise control, both temporally and spatially. By using focused laser illumination, the free nucleotide can be generated at specific locations within a single cell, outside the cell or in a cell-free medium within the limits of the ability to focus the photolytic illumination.

SUMMARY OF THE INVENTION INCLUDING DESCRIPTION OF PREFERRED EMBODIMENTS

Figure 1:
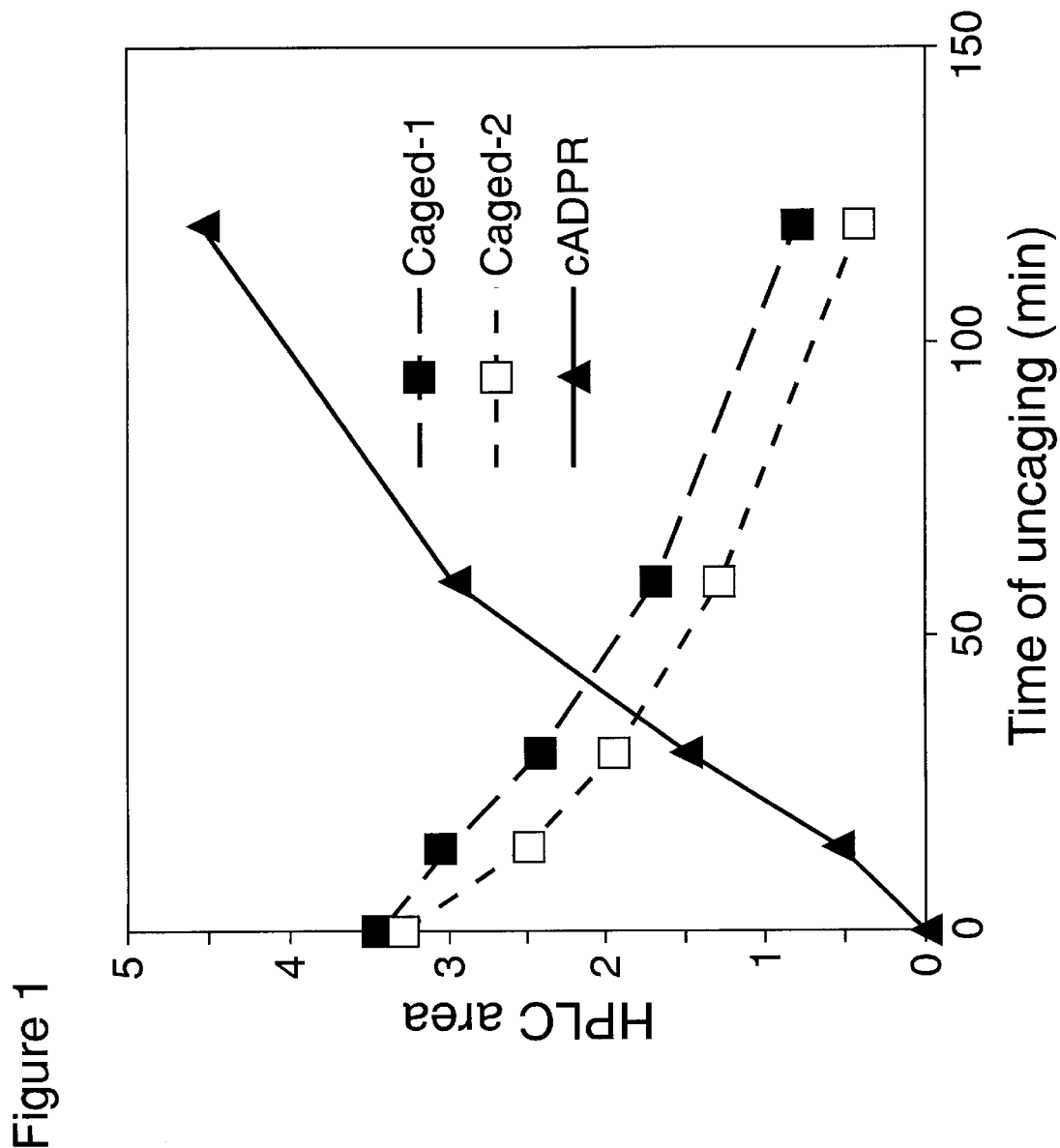
FIG. 1: The time course of uncaging mixed isomers of Compound 1 using a spectrofluorimeter, as described in Example 3.

The present invention comprises a family of photolytically caged nucleotides, including calcium ion mobilizing agents and calcium ion mobilization antagonists. The compounds of the present invention are utilized to release the free nucleotides in aqueous samples upon illumination with precise control both temporally and spatially. The present invention further comprises a method of releasing the free nucleotide in a sample.

Caged Compounds

The caged nucleotides of the present invention have the general formula

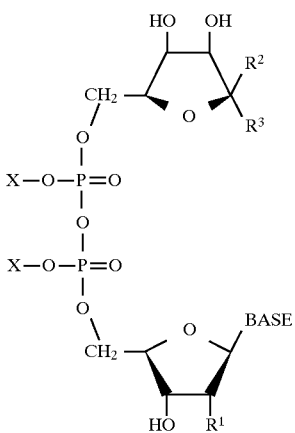

wherein each X is independently H, an alkali metal, an alpha-acyloxyalkyl ester having 3–6 carbons, or a photolabile caging group.

The sugar substituent $R^1$ is H, OH, or $R^1$ has the formula

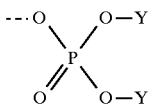

where each Y moiety is independently H, an alkali metal, an alph-acyloxyallyl ester having 3–6 carbons, or a photolabile caging group. For those embodiments wherein $R^1$ is H, the nucleotide is a deoxyribonucleotide. For those embodiments wherein $R^1$ is OH, the nucleotide is a ribonucleotide. For those embodiments wherein $R^1$ is a substituted phosphate, the nucleotide is a phosphoribonucleotide diphosphate.

The $R^2$ substituent is H, $R^3$ is a nicotinamide or nicotinic acid or reduced nicotinamide or nicotinic acid having the formula

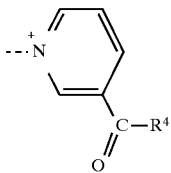

or the formula

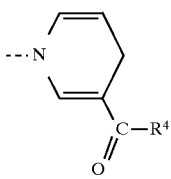

The carbonyl substituent $R^4$ is one of —$NH_2$ (yielding nicotinamide or dihydronicotinamide), OH (yielding nicotinic acid or dihydronicotinic acid) or OZ, where Z is H, an alpha-acyloxyalkyl ester having 3–6 carbons, an alkali metal, a t-butyl group, or a photolabile caging group. Alternatively, $R^3$ is H, OH, or is a single covalent bond with BASE, yielding a cyclic nucleotide.

BASE is a purine or pyrimidine base. Preferably, BASE is selected from adenine (A), guanine (G), hypoxanthine (H), thymine (T), uracil (U) or cytosine (C). The BASE moiety is unsubstituted, or one of the aromatic carbon atoms of BASE is optionally substituted by $NH_2$, SH, Cl, Br, I, F or $N_3$. The BASE moiety is optionally a terminal base, or one of the nitrogens of BASE, in combination with $R^3$, forms single covalent bond resulting in a cyclic nucleotide. The structures of the preferred BASE moieties are shown below.

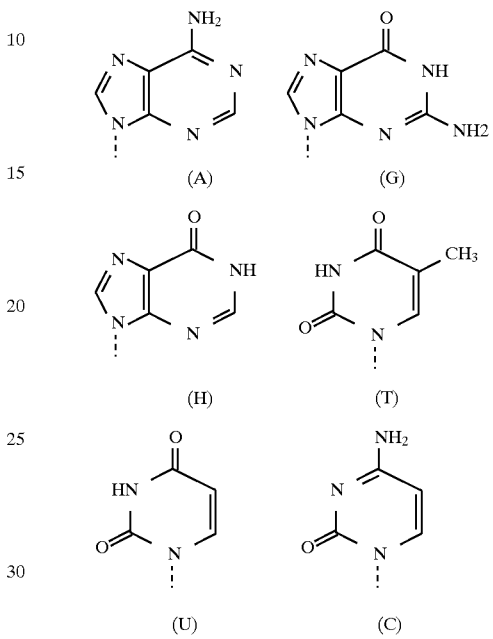

Typically, the BASE of the present invention is a purine base, preferably adenine, guanine or hypoxanthine, more preferably adenine. Where the BASE is optionally substituted by $NH_2$, SH, Cl, Br, I, F or $N_3$, preferably the substituent is one of Br, $NH_2$ or $N_3$, more preferably BASE is substituted by $NH_2$.

The use of alpha-acyloxyalkyl ester to protect carboxylic acid groups is known in the art to improve the solubility of the protected compound in organic solvents. In addition, the alpha-acyloxyalkyl ester protected compound more freely penetrates cellular membranes, where intracellular esterases cleave the esters hydrolytically, producing the free carboxylic acid or phosphate within the cell. Preferably, the alpha-acyloxyalkyl ester is an acetoxymethyl ester ($CH_3CO_2CH_2$—) or pivaloyloxymethyl ester (($CH_3)_3CCO_3CH_2$—). Acetoxymethyl esters of phosphates have been prepared previously (Schultz et al. J. BIOL. CHEM. 268, 6316 (1993)). In one embodiment of the invention, every X or Y that is not a photolabile cage is an alpha-acyloxyalkyl ester.

For all embodiments of the invention, at least one of X, Y or Z is a photolabile caging group. By photolabile caging group is meant any chemical moiety that prevents or reduces the biological activity of the caged nucleotide, that upon illumination, releases the free nucleotide. A preferred caging group is one that maximally interferes with said biological activity. Preferably, one of X is a photolabile caging group. Optionally, any combination of X, Y and Z moieties are photolabile caging groups.

In one embodiment of the invention, the photolabile caging group bound is a derivative of o-nitroarylmethine having the formula:

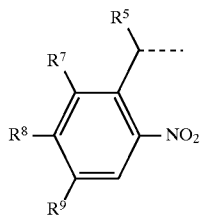

where $R^5$ is one of H, $CH_3$, or $CO_2R^6$, where $R^6$ is H, an alpha-acyloxyalkyl ester having 3–6 carbons, a t-butyl group or an alkali metal. $R^7$ is one of H or $NO_2$. $R^8$ and $R^9$ are independently H, alkoxy having 1–6 carbons, $-O(CH_2)_n CO_2R^{10}$ (where n=1–18 and $R^{10}$ is H or alkyl having 1–6 carbons) or $R^8$ taken in combination with $R^9$ is methylenedioxy ($-O-CH_2-O-$). Caging moieties that are alpha-carboxy nitroarylmethines (compounds wherein $R^5$ is $CO_2R^6$) have been previously described in U.S. Pat. No. 5,635,608 to Haugland et al. (1997) (incorporated by reference). In one embodiment of the invention, $R^5$ is $CH_3$ and $R^7$ is H. In another embodiment of the invention, $R^8$ and $R^9$ are each methoxy.

In another embodiment of the invention, the photolabile caging group is a 2-methoxy-5-nitrophenyl having the formula

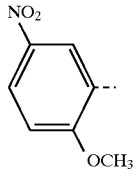

In another embodiment of the invention, the photolabile caging group is a derivative of desyl having the formula:

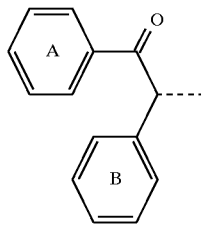

Aromatic rings A and B are optionally and independently substituted one or more times by halogen, $-NO_2$, $-OR^{11}$, and $-NR^{12}R^{13}$ where $R^{11}$, $R^{12}$ and $R^{13}$ are independently alkyl groups having 1–6 carbons. Preferably there are no more than two non-hydrogen substituents on each of rings A and B.

In one embodiment, the caged nucleotide of the invention is a non-cyclized nucleotide having the formula

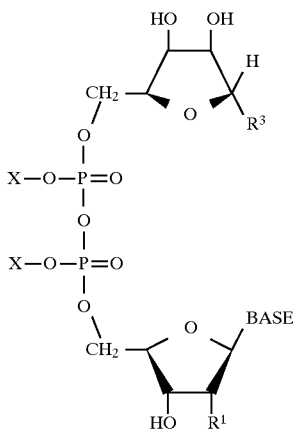

Preferably, where the caged nucleotide is acyclic, the nucleotide is $NAD^+$, NADH, NADP, NADPH, NAADP, or a derivative thereof resulting from the substitution of another purine or pyrimidine base for adenine, preferably guanine or hypoxanthine.

Where the BASE is guanine or hypoxanthine and $R^3$ is nicotinamide or nicotinic acid, the resulting acyclic nucleotide is essentially nonfluorescent, but becomes fluorescent upon cyclization (as described for cGDPR, Graeff et al. J. BIOL. CHEM. 269, 30260 (1994)). These compounds are therefore useful as probes for the activity of various ribosyl cyclase and hydrolase enzymes.

In another embodiment, the caged nucleotide of the invention is a cyclized nucleotide having the formula

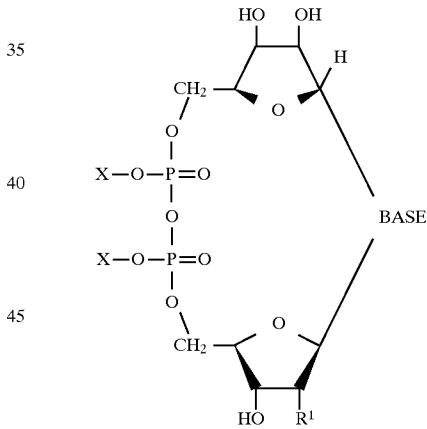

Preferably, where the caged nucleotide is cyclic, the nucleotide is cyclic-ADPR, a cyclic-ADPR antagonist, or a derivative thereof resulting from the substitution of another purine or pyrimidine base for adenine, preferably guanine or hypoxanthine. Where BASE is adenine that is substituted at the 8-position by halogen, SH, $NH_2$ or $N_3$, the resulting compound is a cADPR antagonist (Walseth et al. BIOCHIM. BIOPHYS. ACTA. 1178, 235 (1993), U.S. Pat. No. 5,486, 604 to Walseth et al. (1996). Preferably, the substituted adenine is 8-bromoadenine, 8-aminoadenine or 8-azidoadenine, more preferably 8-amino adenine.

Synthesis of Materials

Where X is used in the following nomenclature, any purine or pyrimidine base is allowed (A, G, T, etc.).

Conversion of nicotinamide to nicotinic acid: Free (uncaged) NAXDP is readily prepared from NXDP by treating with alkaline solution, thereby converting the nicotinamide moiety on NXDP to a nicotinic acid group (as described for NADP in Lee et al. J. BIOL. CHEM. 270 5, 2152 (1995) supra).

cXDPR: The cyclic structure of cXDPR can be visualized as formed by linking $NXD^+$ to the terminal ribose, displacing the nicotinamide group. cXDPR is prepared via two synthetic routes. In the first method, $NAD^+$ (commercially available) or a desired $NAD^+$ analog is incubated with a ribosyl cyclase enzyme, such as produced by Aplysia (as described in Strumwasser et al. U.S. Pat. No. 5,393,667; Lee, et al. CELL REGULATION 2, 203 (1991)) or isolated from other sources (Gu et al. J. AM. CHEM. SOC. 116, 7481 (1994)), and purifying the resulting mixture by high pressure liquid chromatography (HPLC), generating cXDPR. Alternatively, the $NAD^+$ or $NAD^+$ analog is cyclized stereoselectively using a purely synthetic method (treatment with NaBr in DMSO), as described by Yamada et al. for cADPR (J. AM. CHEM. SOC. 116, 10787 (1994)).

Substituted BASE Analogs: Caged nucleotides having substituted BASE moieties (such as cADPR antagonists) are prepared by the substitution of an appropriately substituted $NAD^+$ analog in the preparation of the nucleotide. A variety of substituted bases are commercially available, or are readily prepared using existing methodology. Once the substituted base is prepared, it is converted to the corresponding nucleotide phosphate, and chemically coupled to β-nicotinamide mononucleotide (β-NMN) using carbodiimine coupling. As an example, appropriately substituted 8-substituted adenine monophosphate AMP is chemically coupled to β-nicotinamide mononucleotide (β-NMN) using carbodiimide coupling. The resulting 8-substituted $NAD^+$ is then incubated with ADP-ribosyl cyclase. 8-Amino AMP is derived from 8-azido AMP by treating with dithiothreitol, as described by Walseth et al. (supra). 8-Br AMP, 8-azido AMP and nicotinamide mononucleotide are commercially available (Sigma Chemical Co., St. Louis, Mo.). 8-Mercaptonucleotides are prepared from 8-Br-AMP by reaction with thiourea.

Nitrophenyl Caging Procedure: The relative insensitivity toward acid possessed by the nucleotide diphosphates of the invention allows the phosphate groups of the nucleotide to be coupled to photolabile caging groups, using the method described in Example 1. While in principle both cXDPR and NAXDP offer multiple phosphates where the caging group may be attached (two phosphates for cXDPR, three phosphates for NAXDP), the presently utilized synthetic method generates predominantly singly caged isomers, which can then be readily separated by HPLC, if desired. The attachment of a caging group to the nicotinic acid group of NAXDP is similarly straightforward. In one embodiment, a DMF solution of NAADP is treated with an excess of diazabicyclo[5.4.0]undec-7-ene (DBU) and 6-nitroveratryl bromide to give the caged nicotinic acid after evaporation and purification of the residue via reverse phase chromatography.

Substitution of alpha-acyloxyalkyl esters: Attachment of an alpha-acyloxyalkyl ester selectively on the nicotinic acid group of NAXDP is analogous to the procedure for attachment of a caging group, excepting for the use of Hunig's base instead of DBU and halomethylcarboxylate in place of the nitroveratryl bromide. Typically, the alpha-acyloxyallyl ester is an acetoxymethyl ester, and the halomethylcarboxylate is bromomethyl acetate. The phosphates of the compound of the present invention are also readily derivatized by acetoxymethyl esters using a variation of the method of Schultz et al. (J. BIOL. CHEM. 268, 6316 (1993)), as shown in Example 2.

Desyl Caging Procedure: A desyl caging group is attached to the diphosphates of the nucleotides of the present invention using a method exactly analogous to that described for attaching alpha-acyloxyalkyl esters (above) only using the desired desyl bromide in place of bromomethyl acetate (as described for caged benzoin cAMP, Givens et al. J. AM. CHEM. SOC. 114, 8708 (1992)).

p-Nitroanisole Caging Procedure: The free nucleotide is coupled to 2-methoxy-5-nitrophenol using 1-ethyl-3-(3-dimethylaminopropyl)-carbodiimide hydrochloride (EDAC) (Ramesh et al. PROC. NAT. ACAD. SCI. 90, 11074 (1993)).

Sample Types

The caged nucleotides of the present invention are useful for analyzing the responses of a sample component to the free nucleotide under study. Typically, the sample comprises cells, cell extracts or cell homogenates. The cells present in the sample are optionally plant cells, animal cells or unicellular organisms such as bacteria or yeast cells. The animal cells are optionally invertebrate, amphibian, or mammalian cells. In one embodiment of the invention, the cells of the sample are mammalian cells. Where the caged nucleotides of the invention used in the study of calcium mobilization, the cells are typically sea urchin eggs, neurons, smooth muscle cells, pituitary cells or pancreatic β-cells. In yet another embodiment of the invention, the cells of the sample are egg cells, where the egg cells are fertilized or unfertilized. In a further embodiment of the invention, the cells of the sample are embryonic cells, or blastula cells. Where the sample is an extract or cell homogenate, the sample preferably comprises microsomes originating from the endoplasmic reticulum or vesicles from the sarcoplasmic reticulum. Alternatively, the sample is essentially cell-free, and comprises purified proteins or cell extracts that bind the photoproducts but not the caged nucleotides. Such protein include enzymes and receptor proteins.

Adding the Caged Nucleotide to the Sample

When used as probes for intracellular events, the caged nucleotide is generally introduced into a cell by pressure microinjection methods. Using a microscope (phase contrast) and micromanipulator, the target cell is pierced with a microinjection syringe and the nucleotide is introduced directly into the cytoplasm in a pressurized burst. The volume of injection must usually be less than about 10% of the total cell volume because cells can tolerate only a small increase in volume without disruption of the plasma membrane. In one embodiment, the caged nucleotide is introduced into an egg cell, either before or after fertilization, and the cell is illuminated and therefore uncaged at some point before, during or after cell division. The compounds of the invention are also suitable for use with a variety of cultured cells.

Alternative methods of introducing the nucleotide into the cytoplasm include scrape loading techniques (short mechanical disruption of the plasma membrane where the plasma membrane is peeled away from the cytoplasm, the caged nucleotide is perfused through the sample and the plasma membrane is reassembled), patch clamp methods (where an opening is maintained in the plasma membrane for long periods) or phagocytosis. Any other treatment that will permeabilize the plasma membrane, such as electroporation, shock treatments or high extracellular ATP can be used to introduce the caged nucleotide into the cellular cytoplasm.

For those embodiments of the present invention that are substituted by alpha-acyloxyalkyl esters, or are caged by a photolabile caging group that is substituted by alpha-acyloxyalkyl esters, the caged nucleotide is optionally introduced into living cells by passive permeation through the cellular membranes. Typically, where the probe is not intrinsically water soluble, it is first dissolved in a water miscible solvent such as dimethylsulfoxide (DMSO) to facilitate its dispersion in the biological sample. Nucleotides that are protected by alpha-acyloxyalkyl esters often penetrate cell membranes, and are then cleaved hydrolytically by intracellular esterases, producing a carboxylic acid- or phosphate-substituted nucleotide within the cell.

Where the caged nucleotides of the invention are used as a probe is samples that contain isolated proteins or cell extracts, the probe is generally combined with the sample by simple dissolution, using an organic solvent if necessary to dissolve the probe.

Illumination

After combination with the desired sample, the caged nucleotides of the present invention are photolyzed to cleave the caging group and produce a free nucleotide. This photolytic illumination typically has a wavelength of less than 400 nm, preferably less than 370 nm. Although the photolytic illumination typically has a wavelength greater than 200 nm, in order to prevent damage to biological systems (when present) the illumination preferably has a wavelength greater than 300 nm. The photolytic illumination of compounds of the present invention is completely analogous to photolysis procedures known in the art for other caged probes, and is well known to one of ordinary skill. Illumination of the caged compound within the absorption bands of the photolabile caging group is required, typically using a light source capable of radiation at less than about 400 nm. Typical light sources include mercury arc lamps, flash lamps and lasers such as nitrogen lasers. As analyzed by thin layer chromatography, the caged compounds of the invention are efficiently photolyzed to the free agent even by a hand-held UV lamp. The photolytic illumination is typically generated using an ultraviolet laser. Photolysis of a solution of a compound of the present invention typically produces a mixture of caged and free nucleotides.

Measurement

The determination of the response of the biological sample to the free nucleotide after uncaging will depend upon the nature of the nucleotide, and the nature of the sample. As NAD, NADP, NADH and NADPH are utilized by many cellular processes and enzymatic pathways, the caged probes of the present invention offer opportunities to study a variety of systems.

For example, as NAD pyrophosphate hydrolysis is used to provide the energy for DNA ligase activity (which joins Okazaki fragments in bacteria), one could study the effect on replication by providing a rapid, large influx of NAD in a cell in a time-controlled manner by utilizing a caged NAD of the present invention.

The nucleotides NADH, NAD$^+$ and NADPH (as well as others) are used during glycolysis, the glyoxylate shunt and the TCA cycle (Citric Acid Cycle) and are essential for energy production in cells. These nucleotides are also essential coenzymes for many dehydrogenases, which may bind the nucleotides transiently or essentially permanently. The caged versions of these nucleotides possess utility for investigation of these enzymatic pathways. In particular, the ability to produce a sudden and high level of free NADH in solutions or cells to inhibit the oxidation of pyruvate to acetyl-CoA, preventing entry into the TCA cycle. Similarly, a large and timed influx of NAD can be used to study the process of fatty acid degradation or oxidation. Caged versions of nucleotides that are inhibitors for particular enzymatic pathways are useful for preventing progress along that pathway with spatial and temporal control.

Other NAD-dependent processes that can be studied using the caged nucleotides of the present invention include alcohol metabolism, coupled through alcohol dehydrogenase, and the electron transport system, which also utilizes NADH.

The enzyme cytochrome P-450 catalyzes hydroxylation reactions that require NADH or NADPH as a cofactor. The industrially and scientifically important process of nitrogen fixation requires NADPH. Further, pyrimidine and purine nucleotide biosynthesis requires NADPH (through the use of thioredoxin) to convert ribonucleotides to deoxyribonucleotides. The pentose phosphate pathway (a secondary glucose catabolism pathway) requires NADP. NADPH is required for fatty acid biosynthesis, including steriod biosynthesis. The production of L-ascorbate is via a pathway requiring NADPH. In addition, the reduction of NADP to NADPH is an essential step in the photosynthetic process in plant cells.

For those embodiments of the invention where the caged nucleotide is a calcium mobilization agent, for example, the uncaged nucleotides are useful in activating cell-type specific downstream events that are triggered by elevated $Ca^{2+}$ levels. These events in cells include many that can be studied directly, including, but not limited to such specific cell functions as secretion (pituitary cells, pancreatic β-cells), cortical reaction (egg cells), motility, or contraction (muscle cells). These cell functions are typically easily monitored by visual inspection using standard microscopic techniques known in the art.

The release of $Ca^{2+}$ from intracellular stores is optionally observed directly by the use of a fluorescent or colorimetric calcium ion indicator. Suitable calcium indicators for the purposes of this invention include, but are not limited to Fluo-3, Fura-2, or Indo-1 (available from Molecular Probes, Inc., Eugene Oreg.). Also suitable are the calcium indicators described in U.S. Pat. No. 5,453,517 to Kuhn et al. (1995). Selected embodiments of these indicators are sold under the trade names CALCIUM GREEN, CALCIUM ORANGE and CALCIUM CRIMSON (Molecular Probes, Inc., Eugene Oreg.). Also suitable are the long-wavelength calcium indicators described in U.S. Pat. No. 5,501,980 to Malekzadeh et al. (1996). A specific embodiment of these indicators is sold under the trade name BTC (Molecular Probes, Inc., Eugene Oreg.). An additional useful fluorescent calcium indicator is FURA RED (U.S. Pat. No. 4,849,362 to DeMarinis et al. (1989))

For example, a study of calcium mobilization in sea urchin egg cells is facilitated by the use of caged cADPR (Compound 1). The degree of calcium mobilization in the eggs is optionally monitored either fluorimetrically (using the fluorescent calcium indicator Fluo-3) or visually, by observation of the cortical reaction (CR) of the eggs. The speed of calcium mobilization in the egg cells when using the caged agents is highly dependent upon the intensity and the wavelength of the illumination. Intermittant photolytic illumination will result in a slower uncaging, and therefore slower calcium mobilization, than when the caged probe is uncaged using higher intensity or constant illumination. In particular, when Compoun 1-labeled sea urchin egg cells are photolyzed using a xenon flashlamp that is shuttered on the order of milliseconds, the time required to observe calcium mobilization is reduced to the order of approximately 1 second. The use of the caged agents and antagonists of the present invention therefore allow for the rapid appearance of active agent and antagonist on a very short time scale.

There exists a significant degree of overlap between various releasable $Ca^{2+}$ pools with respect to the ligand induction of $Ca^{2+}$ release. The degree of overlap between different pools is typically investigated by comparing the activities of specific agents and their antagonists. For instance, the inhibition of cADPR-mediated $Ca^{2+}$ release by 8-substituted-cADPR is specific for this ligand, whereas heparin interferes strongly with $IP_3$-mediated $Ca^{2+}$ release and only slightly reduces the rate at which $Ca^{2+}$ is released by cADPR. The photolytically caged cADPR antagonists of the present invention possess specific utility in that the presence of a caged antagonist in a sample allows a calcium mobilization process to be observed, and then halted at any desired point simply by illuminating the sample and thereby releasing the free antagonist.

The mobilizing agent NAADP itself acts as an antagonist for $Ca^{2+}$ release when free NAADP is present within the cell for a time sufficient for the $Ca^{2+}$ response mechanism to become desensitized to NAADP, whereupon NAADP itself becomes an antagonist for further NAADP response. The ability of the present invention to produce a small amount of NAADP in a sample only when desired overcomes this difficulty, as it is no longer necessary to saturate the cell with the free agent in order to study the NAADP induced $Ca^{2+}$ mobilization response.

The examples below are given so as to illustrate the practice of this invention. They are not intended to limit or define the entire scope of this invention.

EXAMPLES

Example 1

Preparation of 1-(2-nitrophenyl)ethyl ester of cyclic-ADP-ribose (Compound 1):

Cyclic-ADP-ribose is synthesized by the incubation of $NAD^+$ with Aplysia ADP-ribosyl cyclase, and purified by HPLC using an AG MP-1 column (as described by Lee, et al., CELL REGULATION, 2, 203 (1991)). The purified cADPR (48 mg, 0.092 mmol) is dissolved in 3 mL of ice-cold E-pure water, and the pH is titrated to 2.3. To the stirring solution is added 2-nitrophenethyldiazoethane (0.28 mmol) (as described by Walker et al., J. AM. CHEM. SOC. 110, 1710 (1988)) in 3 mL of diethyl ether. The resulting biphasic mixture is vigorously stirred at 0.5° C. in darkness for 3 hours, during which the diazoethane solution color changes from amber to pale yellow. The ether layer is drawn off, and the diazoethane/ether treatment is repeated three more times. The aqueous portion is applied to a SEPHADEX LH-20 resin column (2×20 cm), eluting with water, and 2 mL fractions are collected. The caged product (TLC using silica gel: $R_f$0.55 MeOH/$CHCL_3$/$H_2$O/AcOH 12.5:10:3.5:0.2) is isolated as a fluffy white powder after lyophilization of the combined product fractions (30 mg, 49%). Unreacted cADPR is also recovered ($R_f$0.3, 15 mg, 31%). As described above, the caged product consists of a mixture of two mono-caged isomers, which can be separated, if desired, by anion exchange HPLC. For the isomer mixture: m.p. 186° C. (dec.); ε 17,200 (0.8 mM, $H_2O$, 259 nm); $^1$H NMR ($d_6$-DMSO) 9.1–8.6 ppm (m, 2H), 8.0–7.5 ppm (m, 4H), 6.1–5.8 ppm (m, 4H), 4.4 ppm (m, 3H), 4.9 ppm (m, 1H), 4.5–3.8 ppm (m, 10H), 1.65 ppm (m, 2H), 1.50 ppm (dd, J=18.4, 6.5 Hz, 1H). Elemental analysis: C, 38.42%; H, 3.94%; N, 10.89%, which compares well with the expected values: C, 39.05%; H, 4.27%; N, 11.88%, based on the formula of mono-caged cADPR $C_{23}H_{28}N_6O_{15}P_2 \cdot H_2O$.

HPLC separation is performed with columns packed with the AG MP-1 resin (Bio-Rad) and eluted with a nonlinear gradient of trifluoroacetic acid (TFA) similar to that described previously (Lee, et al. J. BIOL. CHEM., 264, 1608 (1989)). Compound 1 is dissolved in $d_6$-DMSO and analyzed with a 400 MHz NMR spectrometer (Bruker AM400).

Example 2

Preparation of a 1-(2-nitrophenyl)ethyl ester of cyclic-ADP-ribose, acetoxymethyl (AM) ester (Compound 2):

The method of Schultz et al. (J. BIOL. CHEM. 268, 6316 (1993)) for preparation of phosphate AM esters is adapted as follows: Compound 1 (1.0 mg, 0.0015 mmol) is suspended in dry acetonitrile (0.5 mL) at room temperature under air. Diisopropylethylamine (2.0 μL, 0.01 mmol) is added, resulting in partial dissolution of the nucleotide. Bromomethyl acetate (1.1 μL, 23 mmol, distilled) is added, and the resulting colorless mixture is stirred at room temperature in darkness for 24 hours. Formation of the phosphate AM ester is evidenced by a higher $R_f$ on analytical TLC (silica gel): $R_f$0.87 for product; $R_f$0.78 for starting material (methanol:chloroform:water:acetic acid, 12.5:10:3.5:0.2). The volatiles are removed under a stream of argon, followed by drying in vacuo to give 1.5 mg of colorless powder.

A desyl-caged nucleotide is prepared using a method analogous to that described above, only using desyl bromide or an appropriately substituted desyl bromide in place of bromomethyl acetate.

Example 3

Photolysis of Compound 1 using a spectrofluorimeter:

A mixture of caged isomers, prepared as in Example 1, is subjected to photolysis in a spectrofluorimeter, by illuminating at 350 nm. The time course of the photolysis is recorded by examining the mixture using anion exchange HPLC, and integrating the area under the HPLC peaks that correspond to the two caged cADPR isomers (Caged-1 and Caged-2) as well as free cADPR itself. As shown in FIG. 1, photolysis is nearly complete in two hours, even when accomplished by the relatively low-power illumination available when using a spectrofluorimeter.

Example 4

Measurement of $Ca^{2+}$ release in cell homogenates:

Homogenates of sea urchin egg (*Stronglocentrotus purpuratus*) are prepared as described previously (Clapper et al., J. BIOL. CHEM. 262, 9561 (1987); Lee, J. BIOL. CHEM. 268, 293 (1993)). Frozen egg homogenates (25%) are thawed at 17° C. for 20 min and diluted to 5% with a medium containing 250 mM N-methylglucamine, 250 mM potassium gluconate, 20 mM Hepes, 1 mM $MgCl_2$, 2 U/ml of creatine kinase, 8 mM phosphocreatine, 0.5 mM ATP, and the fluorescent calcium indicator Fluo-3 at a concentration of 3 mM, at a pH of 7.2 adjusted with acetic acid. The egg homogenates are diluted to 2.5% and finally 1.25% with the medium described, with incubation at 17° C. for one hour between dilutions. $Ca^{+2}$ release is measured by observing spectrofluorimetrically the fluorescence response of Fluo-3 in 1.25% homogenates, using an excitation wavelength of 490 nm and emission wavelength of 535 nm. The measurements are taken in a cuvette maintained at 17° C. and the homogenates are continuously stirred. The volume of homogenate used is 0.2 mL, and additions are usually made in 2 μL volumes.

13

Figure 3:
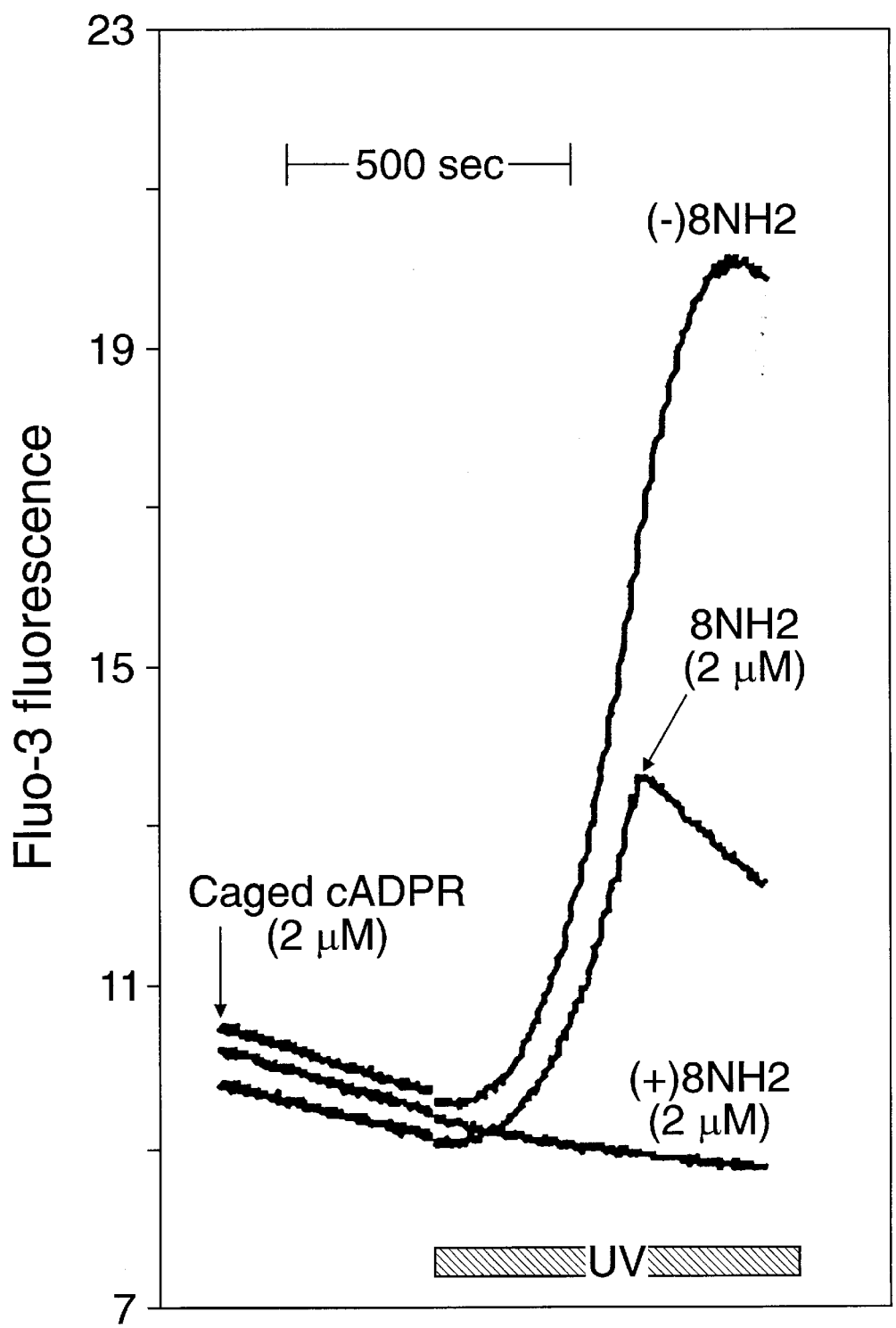
FIG. 3: Calcium release induced by photolysis of Compound 1 in egg homogenates, blocked by the presence of a cADPR antagonist, as described in Examples 4 and 6. Compound 1 is added to the concentration indicated, and the egg homogenate is photolyzed.

Activation of caged cADPR in egg homogenates is achieved in a Hitachi spectrofluorimeter (S-2000) by alternating the excitation wavelength every two seconds between 350 nm for photolysis and 490 nm for monitoring Fluo-3 fluorescence, as shown in FIG. 3. Photolysis of caged cADPR in individual eggs is performed by modifying the epi-fluorescence attachment of a Nikon inverted fluorescence microscope. A second mercury lamp is attached at 90° to the epi-fluorescence tube. The light of 300–400 nm for photolysis is selected with a UG1 filter (Omega Optical, Calif.) and reflected 90°, first with a 400 DCLP dichroic filter and then directed toward the objective with a second BCECF Sp dichroic filter. For monitoring the Fluo-3 fluorescence, 490 nm light from the first mercury lamp is selected with a 485DF22 filter. The excitation light is passed through the same 400 DCLP dichroic filter and is reflected by the BCECF Sp dichroic filter toward the objective. The Fluo-3 fluorescence is selected by a long pass filter with a 500 nm cutoff and monitored by a SIT camera. This optical arranged allows simultaneous measurement of Fluo-3 fluorescence during photolysis.

The presence of free cADPR antagonist, such as 8-amino cADPR results in complete suppression of the calcium mobilization response (FIG. 3). Further, the later addition of a free antagonist after uncaging is shown to reverse the calcium mobilization response (as shown in FIG. 3).

The analogous experiment is performed using a caged NAADP, and results in similar calcium mobilization response.

Example 5

Figure 2:
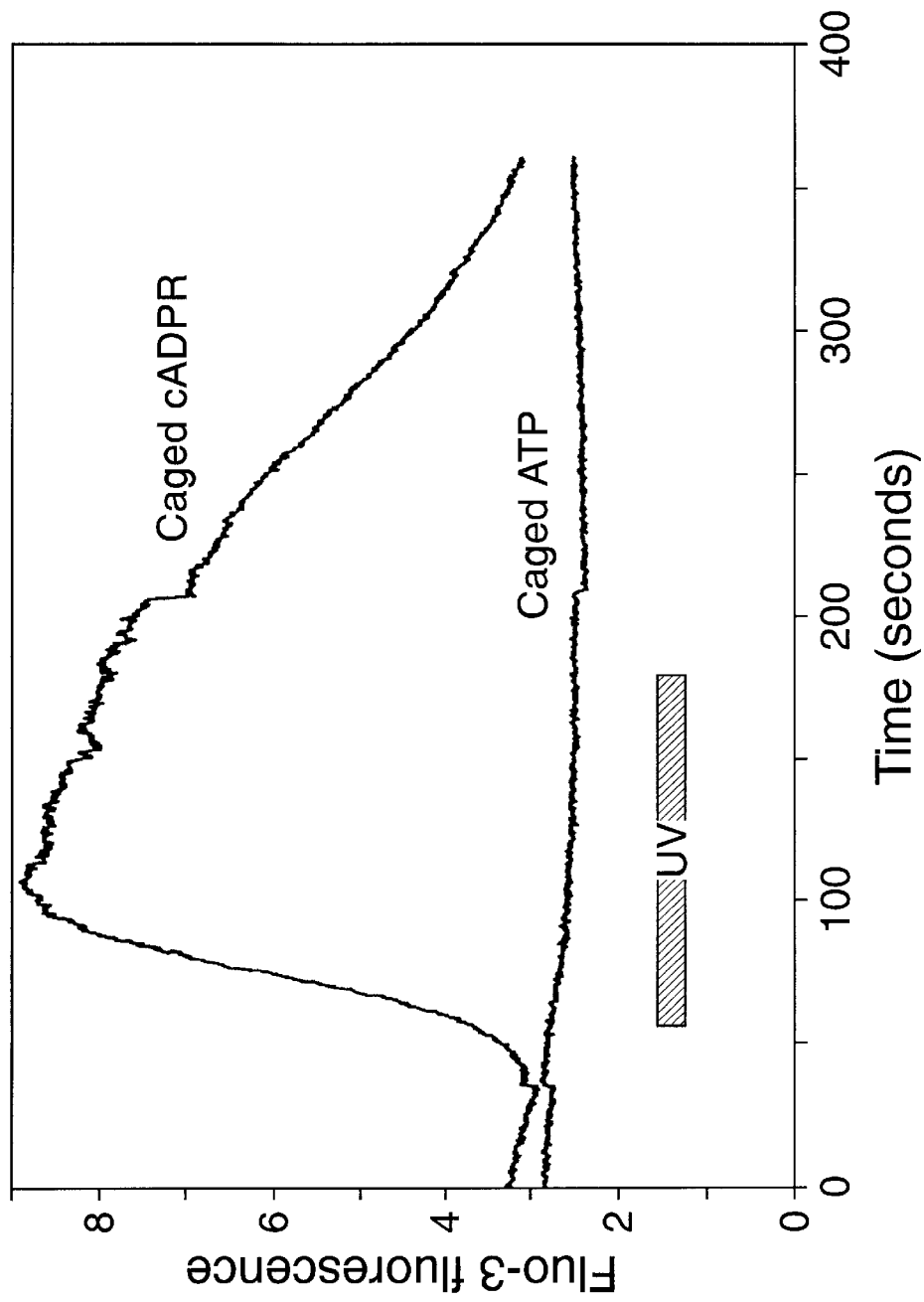
FIG. 2: Calcium release induced by photolysis of Compound 1 in live sea urchin eggs, as described in Example 5.

Measurement of Ca$^{+2}$ release in intact eggs:

*Lytechinus pictus* eggs are used for the microinjection experiments. Ca$^{2+}$ release in individual eggs was monitored by Fluo-3 fluorescence. Compound 1 (~4.9 µM, intracellular) or caged ATP (~7.2 µM, intracellular) is co-injected with Fluo-3 (~0.25 mM, intracellular) into an egg. The injection volumes are about 1.8–2.5% of the egg. All the samples are dissolved in an injection buffer containing 0.5M KCl, 50 µM EGTA, 10 mM Hepes, pH 6.7. The procedures for microinjection by pressure are as described previously (Lee et al., SCIENCE 261, 352 (1993); Dargie et al., CELL REGULATION, 1, 279 (1990)). Photolysis is induced by UV light at around 360 nm. Ca$^{+2}$ changes in the injected eggs are then measured using Fluo-3. As shown in FIG. 2, upon UV illumination, Ca$^{2+}$ release is clearly observed when Compound 1 is present in the egg cell.

The analogous experiment is performed using a caged NAADP, resulting in similar calcium mobilization response.

It is to be understood that, while the foregoing invention has been described in detail by way of illustration and example, numerous modifications, substitutions, and alterations are possible without departing from the spirit and scope of the invention as described in the following claims.

14

What is claimed is:

1. A compound of the formula

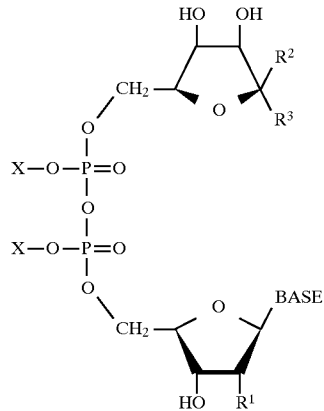

wherein
each X is independently H, an alkali metal, an alpha-acyloxyalkyl ester having 3–6 carbons, or a photolabile caging group;
R$^1$ is H, OH, or

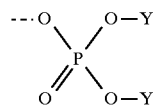

where each Y is independently H, an alkali metal, an alpha-acyloxyalkyl ester having 3–6 carbons, or a photolabile caging group;
R$^2$ is H;
R$^3$ is H or R$^3$ is a single covalent bond with BASE, yielding a cyclic nucleotide; or R$^3$ is

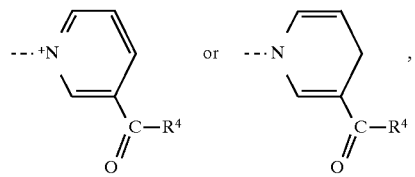

where R$^4$ is NH$_2$, OH or OZ, where Z is H, an alpha-acyloxyalkyl ester having 3–6 carbons, an alkali metal, a t-butyl group, or a photolabile caging group;
BASE is a purine base that is unsubstituted or optionally substituted by NH$_2$, SH, Cl, Br, I, or N$_3$;
such that there must be at least one X, Y or Z that is a photolabile caging group.

2. A compound as claimed in claim 1, wherein said photolabile caging group has the formula

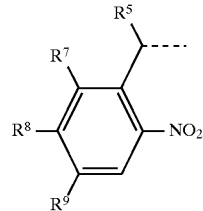

wherein

R⁵ is H, CH₃, or CO₂R⁶, where R⁶ is H, an alpha-acyloxyalkyl ester, a t-butyl group or an alkali metal;

R⁷ is H or NO₂;

R⁸ and R⁹ are independently H, alkoxy having 1–6 carbons, —O(CH₂)$_n$CO₂R¹⁰, wherein n=1–18 and R¹⁰ is H or alkyl having 1–6 carbons, or R⁸ taken in combination with R⁹ is methylenedioxy, —O—CH₂—O—;

or the formula

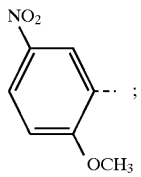

or the formula

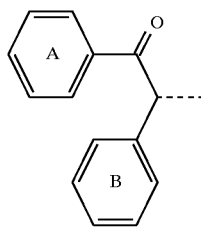

wherein aromatic rings A and B are optionally and independently substituted one or more times by halogen, —NO₂, —OR¹¹, and —NR¹²R¹³ where R¹¹, R¹² and R¹³ are independently alkyl groups having 1–6 carbons.

3. A compound, as claimed in claim 1, wherein said photolabile caging group has the formula

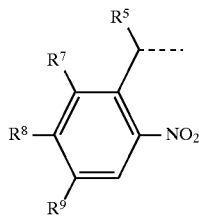

4. A compound, as claimed in claim 3, wherein R⁵ is H or CH₃, R⁷ is H or NO₂, and R⁸ and R⁹ are H or methoxy.

5. A compound, as claimed in claim 1, wherein each alpha-acyloxyalkyl ester is an acetoxymethyl ester or pivaloyloxymethyl ester.

6. A compound as claimed in claim 1, wherein BASE is an adenine, guanine or hypoxanthine, wherein one of the carbon atoms of said BASE is optionally substituted by NH₂, SH, Cl, Br, I or N₃.

7. A compound, as claimed in claim 6, wherein BASE is an adenine.

8. A compound, as claimed in claim 7, wherein BASE is an 8-aminoadenine, an 8-bromoadenine 8-mercaptoadenine or 8-azidoadenine.

9. A compound, as claimed in claim 1, wherein exactly one of X, Y or Z is a photolabile caging group, and each remaining X, Y or Z is an acetoxymethyl ester or H.

10. A compound, as claimed in claim 9, wherein exactly one X is a photolabile caging group.

11. A compound, as claimed in claim 1, wherein R³ is

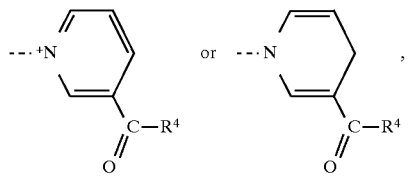

where R⁴ is NH₂, OH or OZ, where Z is H, an alpha-acyloxyalkyl ester having 3–6 carbons, an alkali metal, or a t-butyl group.

12. A compound, as claimed in claim 1, wherein

R¹ is H or OH;

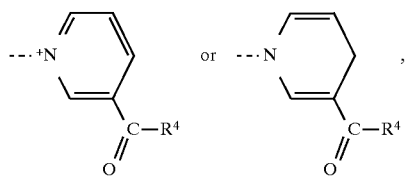

and said photolabile caging group has the formula

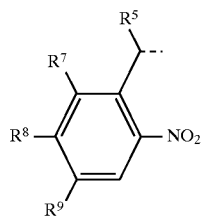

wherein

R⁵ is H, CH₃, or CO₂R⁶, where R⁶ is H, an alpha-acyloxyalkyl ester, a t-butyl group or an alkali metal;

R⁷ is H or NO₂;

R⁸ and R⁹ are independently H, alkoxy having 1–6 carbons, —O(CH₂)$_n$CO₂R¹⁰, where n=1–18 and R¹⁰ is H or alkyl having 1–6 carbons, or R⁸ taken in combination with R⁹ is methylenedioxy, —O—CH₂—O—;

or the formula

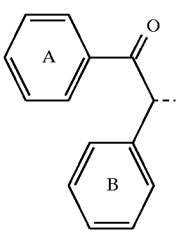

wherein aromatic rings A and B are optionally and independently substituted one or more times by halogen, —NO₂, —OR¹¹, and —NR¹²R¹³ where R¹¹, R¹² and R¹³ are independently alkyl groups having 1–6 carbons.

13. A compound, as claimed in claim 12, wherein BASE is an adenine.

14. A compound, as claimed in claim 1, having the formula

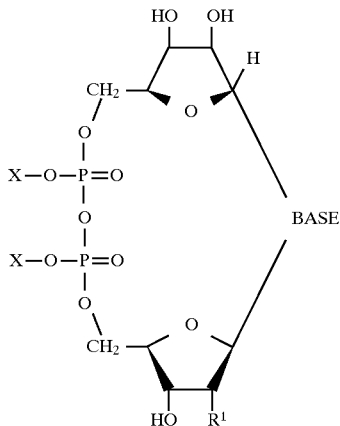

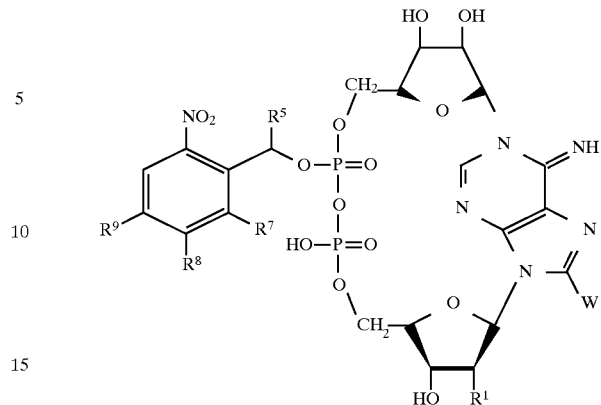

15. A compound, as claimed in claim 14, wherein said photolabile caging group has the formula

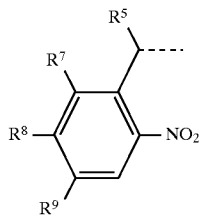

wherein
  $R^5$ is H, $CH_3$, or $CO_2R^6$, where $R^6$ is H, an alpha-acyloxyalkyl ester, a t-butyl group or an alkali metal;
  $R^7$ is H or $NO_2$;
  $R^8$ and $R^9$ are independently H, alkoxy having 1–6 carbons, $-O(CH_2)_nCO_2R^{10}$, where n=1–18 and $R^{10}$ is H or alkyl having 1–6 carbons, or $R^8$ taken in combination with $R^9$ is methylenedioxy, $-O-CH_2-O-$;
or the formula

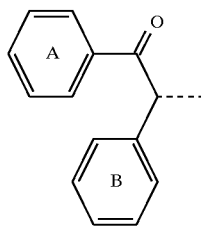

wherein aromatic rings A and B are optionally and independently substituted one or more times by halogen, $-NO_2$, $-OR^{11}$, and $-NR^{12}R^{13}$ where $R^{11}$, $R^{12}$ and $R^{13}$ are independently alkyl groups having 1–6 carbons.

16. A compound, as claimed in claim 15, wherein BASE is an adenine, guanine, or hypoxanthine.

17. A compound, as claimed in claim 1, having the formula or the formula

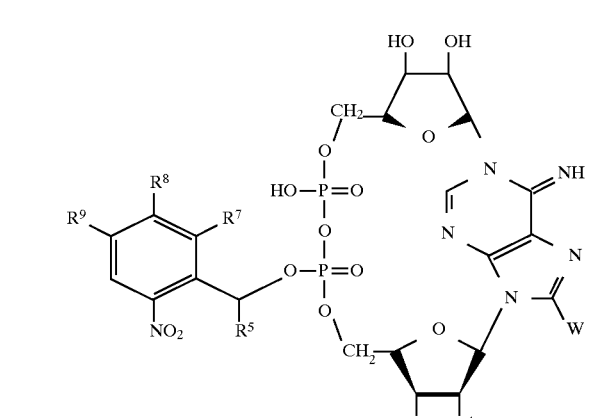

wherein
  $R^1$ is H, OH, or

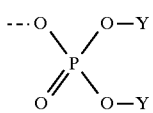

where each Y is independently H, an alkali metal, or an alpha-acyloxyalkyl ester having 3–6 carbons;
  $R^5$ is H or $CH_3$;
  $R^7$ is H or $NO_2$;
  $R^8$ and $R^9$ are independently H or alkoxy having 1–6 carbons; and
  W is H, $NH_2$, SH, Cl, Br, I or $N_3$.

18. A method for obtaining a free nucleotide compound in a sample by subjecting said sample to illumination, comprising:

a) adding to a sample a compound of the formula

[chemical structure showing nucleotide with HO, OH, R², R³, CH₂, O, X—O—P=O, X—O—P=O, O, CH₂, BASE, HO, R¹]

wherein each X is independently H, an alkali metal, an alpha-acyloxyalkyl ester having 3–6 carbons, or a photolabile caging group;

R¹ is H, OH, or

[structure: ---O, O—Y, P=O, O, O—Y]

where each Y is independently H, an alkali metal, an alpha-acyloxyalkyl ester having 3–6 carbons, or a photolabile caging group;

R² is H;

R³ is H or R³ is a single covalent bond with BASE, yielding a cyclic nucleotide; or R³ is

[pyridinium and pyridine structures with C—R⁴ / =O]

where R⁴ is $NH_2$, OH or OZ, where Z is H, an alpha-acyloxyalkyl ester having 3–6 carbons, an alkali metal, a t-butyl group, or a photolabile caging group;

BASE is a purine base that is unsubstituted or optionally substituted by $NH_2$, SH, Cl, Br, I or $N_3$;

such that there must be at least one X, Y or Z that is a photolabile caging group;

and ii) illuminating said sample at a wavelength less than about 400 nm to obtain the free nucleotide compound.

19. A method, as claimed in claim 18, wherein said photolabile caging group has the formula

[aromatic structure with R⁵, R⁷, R⁸, R⁹, $NO_2$]

wherein $R^5$ is H, $CH_3$, or $CO_2R^6$, where $R^6$ is H, an alpha-acyloxyalkyl ester having 3–6 carbons, a t-butyl group or an alkali metal;

$R^7$ is H or $NO_2$;

$R^8$ and $R^9$ are independently H, alkoxy having 1–6 carbons, —$O(CH_2)_nCO_2R^{10}$, where n=1–18 and $R^{10}$ is H or alkyl having 1–6 carbons, or $R^8$ taken in combination with $R^9$ is methylenedioxy, —O—$CH_2$—O—;

or the formula

[aromatic structure with $NO_2$, $OCH_3$]

or the formula

[structure with aromatic rings A and B with C=O]

wherein aromatic rings A and B are optionally and independently substituted one or more times by halogen, —$NO_2$, —$OR^{11}$, and —$NR^{12}R^{13}$ where $R^{11}$, $R^{12}$ and $R^{13}$ are independently alkyl groups having 1–6 carbons.

20. A method, as claimed in claim 18, wherein said sample comprises cells.

21. A method, as claimed in claim 20, wherein said sample comprises mammalian cells.

22. A method, as claimed in claim 18, wherein said sample is essentially cell-free.

23. A method, as claimed in claim 18, wherein said sample is illuminated at a wavelength less than about 370 nm and greater than about 300 nm.

24. A method, as claimed in claim 18, wherein

R³ is

[pyridinium and pyridine structures with C—R⁴ / =O]

where $R^4$ is $NH_2$, OH or OZ, where Z is H, an alpha-acyloxyalkyl ester having 3–6 carbons, an alkali metal, a t-butyl group, or a photolabile caging group; and BASE is an adenine.

25. A method, as claimed in claim 18, wherein said compound has the formula

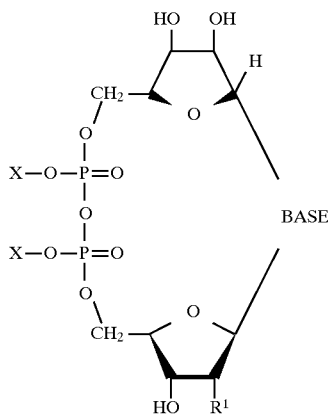

wherein $R^1$ is H, OH, or

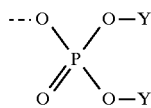

where each Y is independently H, an alkali metal or an alpha-acyloxyalkyl ester having 3–6 carbons; and BASE is an adenine, guanine or hypoxanthine.

26. A method, as claimed in claim 18, wherein said compound has the formula

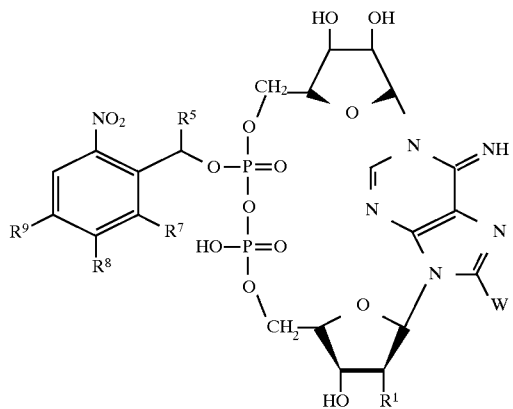

or the formula

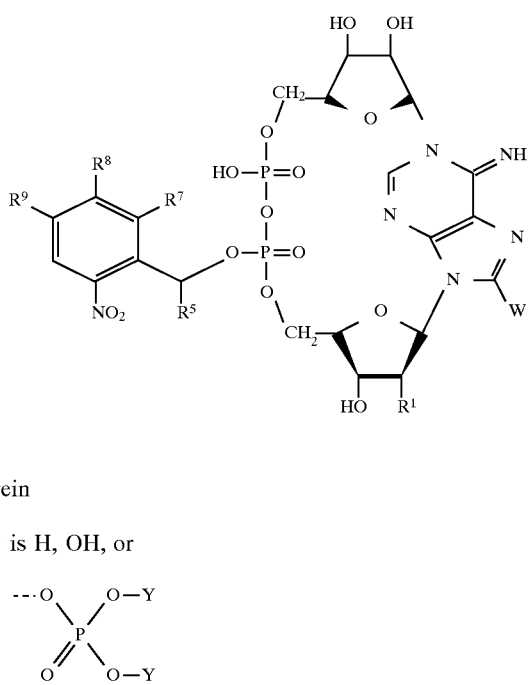

wherein $R^1$ is H, OH, or

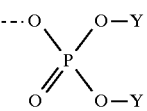

where each Y is independently H, an alkali metal, or an alpha-acyloxyalkyl ester having 3–6 carbons;

$R^5$ is H or $CH_3$;

$R^7$ is H or $NO_2$;

$R^8$ and $R^9$ are independently H or alkoxy having 1–6 carbons; and

W is H, $NH_2$, SH, Cl, Br, I or $N_3$.

27. A compound of the formula

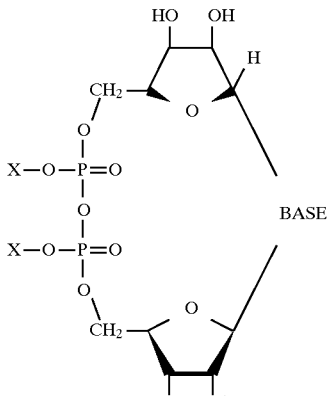

wherein each X is independently H, an alkali metal, or an alpha-acyloxyalkyl ester having 3–6 carbons;

$R^1$ is H, OH, or

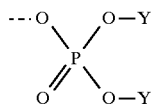
where each Y is independently H, an alkali metal, or an alpha-acyloxyalkyl ester having 3–6 carbons; and
BASE is a guanine or hypoxanthine base that is unsubstituted or optionally substituted by $NH_2$, SH, Cl, Br, I, or $N_3$.
* * * * *

UNITED STATES PATENT AND TRADEMARK OFFICE
CERTIFICATE OF CORRECTION

PATENT NO. : 5,873,243
DATED : February 16, 1999
INVENTOR(S) : Gee et al.

It is certified that error appears in the above-identified patent and that said Letters Patent is hereby corrected as shown below:

<u>Column 11,</u>
Line 59, "Rf0.3" should read -- RF 0.13 --.

<u>Column 16,</u>
Line 20, delete " 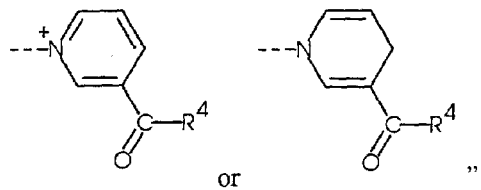 "

Signed and Sealed this

Seventeenth Day of September, 2002

*Attest:*

*Attesting Officer*

JAMES E. ROGAN
*Director of the United States Patent and Trademark Office*